(12) United States Patent
Hiramatsu et al.

(10) Patent No.: US 9,215,975 B2
(45) Date of Patent: Dec. 22, 2015

(54) OPHTHALMIC DEVICE

(75) Inventors: Hiroyuki Hiramatsu, Toyokawa (JP); Kazunari Shimizu, Toyokawa (JP)

(73) Assignee: NIDEK CO., LTD., Gamagori (JP)

( * ) Notice: Subject to any disclaimer, the term of this patent is extended or adjusted under 35 U.S.C. 154(b) by 725 days.

(21) Appl. No.: 13/499,160

(22) PCT Filed: Nov. 11, 2010

(86) PCT No.: PCT/JP2010/070082
§ 371 (c)(1),
(2), (4) Date: Mar. 29, 2012

(87) PCT Pub. No.: WO2011/059018
PCT Pub. Date: May 19, 2011

(65) Prior Publication Data
US 2012/0188357 A1    Jul. 26, 2012

(51) Int. Cl.
*A61B 3/117* (2006.01)
*A61B 3/10* (2006.01)

(52) U.S. Cl.
CPC ............... *A61B 3/1173* (2013.01); *A61B 3/102* (2013.01)

(58) Field of Classification Search
CPC ........ A61B 3/102; A61B 3/00; A61B 3/0091; A61B 3/09; A61B 3/10; A61B 3/1173; H04N 13/0484
USPC .......................................................... 348/78
See application file for complete search history.

(56) References Cited

U.S. PATENT DOCUMENTS

| | | | |
|---|---|---|---|
| 3,525,565 A * | 8/1970 | O'Neill et al. | 351/205 |
| 2001/0026350 A1 * | 10/2001 | Fujieda | 351/212 |
| 2002/0055736 A1 * | 5/2002 | Horn et al. | 606/26 |
| 2004/0230203 A1 | 11/2004 | Yaguchi | |
| 2005/0099600 A1 * | 5/2005 | Frey et al. | 351/205 |

(Continued)

FOREIGN PATENT DOCUMENTS

| | | |
|---|---|---|
| EP | 1138252 A2 | 10/2001 |
| JP | A-2004-337551 | 12/2004 |
| JP | A-2006-116028 | 5/2006 |

(Continued)

OTHER PUBLICATIONS

Taniguchi, S., "Classification of Fragility of Zinn's Zonule Based on Lens Oscillation During Cutting of Anterior Capsule," *Journal of Ophthalmic Surgery*, 2008, p. 218, vol. 22, No. Special Extra Issue (with translation).

(Continued)

*Primary Examiner* — Andy Rao
*Assistant Examiner* — Obafemi Sosanya
(74) *Attorney, Agent, or Firm* — Oliff PLC

(57) ABSTRACT

An ophthalmic device to measure weakness of Zinn's zonule of an examinee's eye having: an illuminating unit arranged to illuminate the examinee's eye including a lens; an imaging unit including an imaging element and arranged to capture an image of an anterior segment illuminated by the illuminating unit; and a determination unit arranged to process the image of the anterior segment captured by the imaging unit after applying a stimulus to guide the lens to move, the determination unit being further configured to obtain positional information of a characteristic point of the lens to detect mobility of the lens relative to the pupil when the lens returns to a pre-stimulus status, and determine the zonular weakness based on the detected mobility.

18 Claims, 6 Drawing Sheets

(56) References Cited

U.S. PATENT DOCUMENTS

2005/0162611 A1* 7/2005 Miwa .................... 351/206
2010/0191226 A1* 7/2010 Blumenkranz et al. ........... 606/4

FOREIGN PATENT DOCUMENTS

| JP | A-2007-37984 | 2/2007 |
| JP | A-2010-12184 | 1/2010 |
| WO | WO 2010/075097 A1 | 7/2010 |

OTHER PUBLICATIONS

International Search Report issued in International Application No. PCT/JP2010/070082 on Jan. 25, 2011 (with translation).
Jan. 7, 2013 Extended European Search Report issued in European Patent Application No. 10829977.7.

* cited by examiner

OPHTHALMIC DEVICE

CROSS-REFERENCE TO RELATED APPLICATIONS

This is a 371 national phase application of PCT/JP2010/070082 filed on Nov. 11, 2010, which claims the benefit of priority from the prior Japanese Patent Application No. 2009-257676 filed on Nov. 11, 2009, the entire contents of which are incorporated herein by reference.

FIELD OF THE INVENTION

The present invention relates to an ophthalmic device used to measure the weakness of Zinn's zonule (zonula ciliaris, zonule) supporting a lens in an eye.

BACKGROUND OF THE INVENTION

A known technique conventionally adopted for a treatment of an eye affected by cataract is to place an intraocular lens in a lens capsule after removal of a clouded nucleus of a crystalline lens ("lens"). For removal of cataractous nucleus of lens, phacoemulsification is used. In cataract operations, the nucleus of lens is emulsified and suctioned to be removed by an ultrasonic tip of a surgical appliance inserted in the lens capsule. The lens is coupled with a ciliary body by the Zinn's zonule. The zonule is composed of a countless number of fibrous tissues which are transparent and very thin. During the cataract operation, the lens is subject to an external force applied by movement of and suctioning by the ultrasonic tip, and a stress accordingly acts on the zonule in a manner that follows the movement of the lens. In the case where the zonule of an eye operated on is weak, the removal of the nucleus of lens involves a risk of complications caused by, for example, dislocation of the lens, and accidental drop of the dislocated lens in a vitreous chamber. Patent Document 1 discloses an operation for an eye with weak zonule.

RELATED ART DOCUMENTS

Patent Document

Patent Document 1: JP 2004-337551A

DISCLOSURE OF THE INVENTION

Problem to be Solved by the Invention

Conventionally, an operator himself mostly checks the weakness or fragility of Zinn's zonule in an eye operated on for the treatment of cataract by wobbling the lens using a surgical appliance after the start of the cataract operation. When an eye with weak zonule is operated on, the operator carefully performs the operation with great care and attention to avoid dislocation of the lens. Often, the cataract operation accompanied by such a careful handling may necessitate more time than originally scheduled or may be performed in underprepared circumstances. Therefore, it is most desirable to know beforehand how weak the zonule is. In the case of checking the weakness of the zonule after cutting the lens, it largely depends on an operator's subjective evaluation, leaving little room for objective evaluation.

The present invention has been made to solve the above problems and has a purpose to provide an ophthalmic device configured to easily know the weakness of Zinn's zonule prior to an operation.

Means for Solving the Problem

To achieve the above purpose, the present invention provides the following technical features.

(1) One aspect of the present invention provides an ophthalmic device to measure weakness of Zinn's zonule of an examinee's eye, the device comprising: an illuminating unit arranged to illuminate the examinee's eye including a lens; an imaging unit including an imaging element and arranged to capture an image of an anterior segment illuminated by the illuminating unit; and a determination unit arranged to process the image of the anterior segment captured by the imaging unit after applying a stimulus to guide the lens to move, the determination unit being further configured to obtain positional information of a characteristic point of the lens to detect mobility of the lens relative to the pupil when the lens returns to a pre-stimulus status, and determine the zonular weakness based on the detected mobility.

(2) In the ophthalmic device according to (1), preferably, the determination unit image-processes at least two images of the anterior segment, calculates a moving speed of the lens when returning to the pre-stimulus status based on positional information of characteristic points of the lens in the respective images and a time interval at which the images are captured, and determines the zonular weakness based on the calculated moving speed.

(3) In the ophthalmic device according to (2), preferably, the determination unit obtains at least two images of the anterior segment before and after the movement of the eye caused by the applied stimulus, during the movement of the eye, before and during the movement of the eye, or during and after the movement of the eye.

(4) In the ophthalmic device according to (1), preferably, the determination unit detects the mobility of the lens when returning to the pre-stimulus status based on whether a position of the characteristic point of the lens relative to a predetermined reference position of the pupil is included in a predetermined amount to determine the zonular weakness.

(5) In the ophthalmic device according to (1), preferably, the determination unit processes the image of the anterior segment to obtain a clouded site of the lens as the characteristic point.

(6) In the ophthalmic device according to (1), preferably, the determination unit image-processes at least two images of the anterior segment captured by the imaging unit before and after application of the stimulus and extracts a predetermined characteristic point of the lens in each image to determine the zonular weakness based on whether a positional change of the characteristic point in each image is included in a predetermined amount.

(7) The ophthalmic device according to (1) preferably further includes a memory for storing the image of the anterior segment captured by the imaging unit, the memory storing therein at least two images of the anterior segment before and after the movement of the examinee's eye caused by the applied stimulus, during the movement of the examinee's eye, before and during the movement of the examinee's eye, or during and after the movement of the examinee's eye, wherein the determination unit image-processes the images of the anterior segment stored in the memory to obtain positional information of the characteristic point of the lens, and detects the mobility of the lens relative to the pupil when the lens returns to the pre-stimulus status.

(8) The ophthalmic device according to (1) preferably further includes a stimulus applying unit arranged to apply the stimulus to guide the lens to move.

(9) In the ophthalmic device according to (8), preferably, the stimulus applying unit includes a fixation target presenting unit having a fixation target for guiding a visual axis of the examinee's eye, the fixation target presenting unit being configured to switch the fixation target between a first direction and a second direction different from the first direction.

(10) The ophthalmic device according to (1) preferably further includes: an eye opening detecting unit arranged to detect opening of the examinee's eye after blinking of the eye based on the image of the anterior segment captured by the imaging unit, and an image obtaining unit arranged to obtain the image of the anterior segment after application of the stimulus based on a detection signal outputted from the eye opening detecting unit.

(11) In the ophthalmic device according to (1), preferably, the imaging unit has an optical axis for capturing an image of the examinee's eye from a direction straight ahead of the eye, and the imaging unit obtains a diaphanoscopic image in which the lens is illuminated from behind by illumination light of the illuminating unit or an image of the anterior segment in which the lens is illuminated from a direction straight ahead of the examinee's eye by the illumination light of the illuminating unit as the image of the anterior segment.

(12) In the ophthalmic device according to (1), preferably, the illuminating unit includes an illumination light source and a slit aperture to project slit light on the lens of the examinee's eye, and the imaging unit has an optical axis for capturing an image of the examinee's eye from an oblique direction of the eye and captures a tomographic image of the lens optically cut in cross section by the slit light.

(13) In the ophthalmic device according to (1), preferably, the imaging unit includes an optical coherence tomography device and obtains a tomographic image of the anterior segment including the lens.

Effect of the Invention

According to the present invention, the weakness of Zinn's zonule can be easily known prior to a cataract operation, and the zonular weakness can be quantitatively ascertain without relying on an operator's subjective evaluation.

EMBODIMENTS FOR CARRYING OUT THE INVENTION

Figure 1:
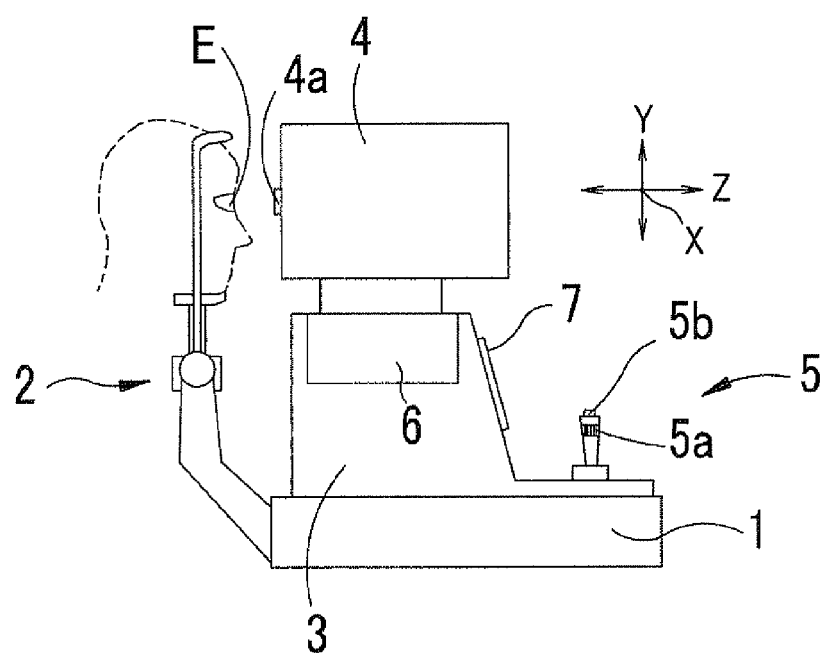
FIG. 1 is an external configuration view of an ophthalmic device in an embodiment.
Figure 2:
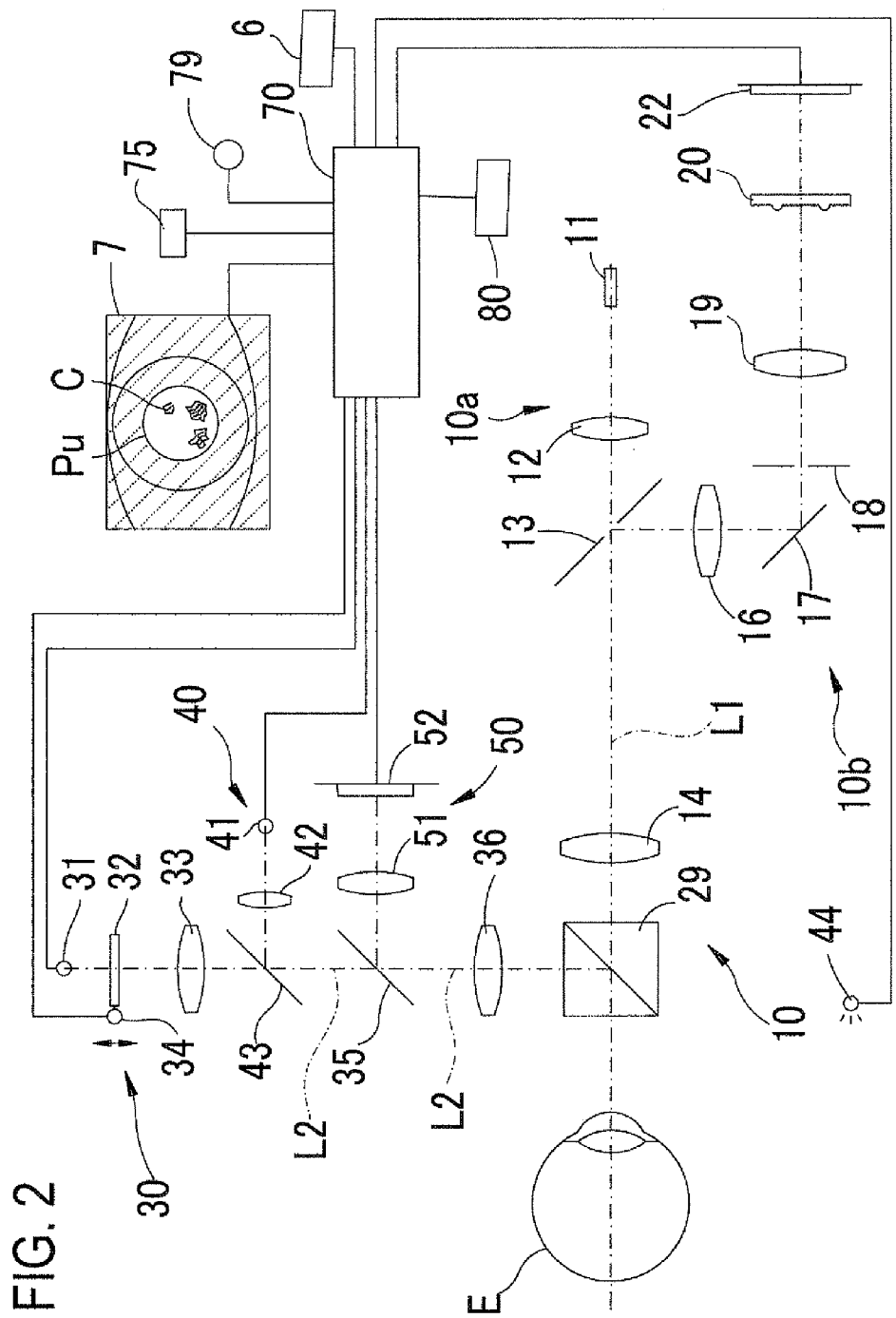
FIG. 2 is a schematic configuration view of optical systems and a control system of the device.

A detailed description of a preferred embodiment of the present invention will now be given referring to the accompanying drawings. FIG. 1 is an external configuration view of an ophthalmic device including an eye refractive power measuring optical system and an imaging optical system (a photographing optical system) configured to image (photograph) an examinee's eye, wherein these optical systems are jointly used to measure the weakness of Zinn's zonule (zonular weakness). FIG. 2 is a schematic configuration view of the optical systems and a control system of the device.

The ophthalmic device has a base table 1, a face support unit 2 attached to the base table 1, a movable table 3 movably provided on the base table 1, and a measuring unit 4 being movably provided on the movable table 3 and containing the optical systems. The measuring unit 4 has a measurement window 4a so that the optical systems provided in the device are positionally adjusted to the examinee's eye through the measurement window 4a. The measuring unit 4 is moved by an XYZ drive unit 6 provided on the movable table 3 in a right-left direction (an X direction), an up-down direction (a Y direction), and a back-forth direction (a Z direction) relative to an examinee's eye E. When a joystick 5 is manipulated, the movable table 3 is moved on the base table 1 in the X direction and the Z direction. When an examiner rotates a rotary knob 5a, the measuring unit 4 is moved in the Y direction according to Y-drive of the XYZ driving unit 6. A measurement start switch 5b is provided at a top of the joystick 5. The movable table 3 is provided with a display 7 for displaying images of the examinee's eye and a measurement result. A cabinet of the measuring unit 4 is positioned in front of the examinee's eyes (the side of the cabinet of the measuring unit 4 facing the examinee is large enough to shield the examinee's eyes). Accordingly, the examinee's pupil is in the state of natural mydriasis in which the pupil is naturally dilated. This helps to ensure a pupil diameter large enough to measure the refractive power. A zonular weakness measurement mode can obtain images capturing an extensive area of a crystalline lens ("lens").

The measuring unit 4 contains an eye refractive power measuring optical system 10, a fixation target presenting optical system 30, an alignment-index projecting optical system 40, an imaging optical system 50, and a controller 70. The measurement optical system 10 has a light projecting optical system 10a configured to project a spot-like measurement index on a fundus via a pupil center part of the examinee's eye E and a photo-receiving optical system 10b configured to receive a reflection light reflected from the fundus.

The projecting optical system 10a positioned on an optical axis L1 includes a measurement light source 11 which emits near-infrared light, a relay lens 12, a hole mirror 13, and an objective lens 14. The light source 11 has a positional relationship optically conjugate with an emmetropic fundus. An opening of the hole mirror 13 has a positional relationship optically conjugate with the pupil of the examinee's eye E. A measurement light flux emitted from the light source 11 passes through the pupil center part and converges on vicinity of the lens of the eye E by the objective lens 14, and is finally projected on the fundus. The projecting optical system 10a is concurrently used as an illuminating optical system to obtain a diaphanoscopic image of the lens.

The photo-receiving optical system 10b shares the objective lens 14 and the hole mirror 13 with the projecting optical system 10a. The photo-receiving optical system 10b includes a relay lens 16 placed in a reflecting direction of the hole mirror 13, a total reflection mirror 17, a photo-receiving diaphragm 18, a collimator lens 19, a ring lens 20, and a two-dimensional imaging element 22. The diaphragm 18 and the imaging element 22 have a positional relationship optically conjugate with the fundus. The ring lens 20 includes a lens part where a cylindrical lens of a ring shape is formed on a transparent flat plate, and a shielding part which is other portion than the ring-shape lens part. The ring lens 20 has a positional relationship optically conjugate with the pupil of the examinee's eye E. The reflection light reflected from the fundus is taken out in a ring shape by the ring lens 20 via a peripheral part of the pupil and received by the imaging element 22. Output from the imaging element 22 is inputted to the controller 70.

A dichroic mirror 29 is placed between the objective lens 14 and the examinee's eye E. The fixation target presenting optical system 30, an alignment-index projecting optical system 40, and an imaging optical system (a photographing optical system) 50 configured to obtain an image the anterior segment of the examinee's eye are provided on the opposite side of the dichroic mirror 29. The alignment-index projecting optical system 40 includes a light source 41 which emits infrared light. This optical system 40 is arranged to project an alignment index on the cornea of the examinee's eye through a lens 42, a half mirror 43, and a lens 36.

The imaging optical system 50 has an optical axis for imaging the examinee's eye from a direction straight ahead of the eye, and includes an imaging lens 51 and a two-dimensional imaging element 52 which are placed on the optical axis in a reflecting direction of the half mirror 35. Output from the imaging element 52 is inputted to the controller 70. For alignment of the examinee's eye, the anterior segment is illuminated by a light source 44. The image of the anterior segment captured by the imaging element 52 is displayed on the display 7.

The fixation target presenting optical system 30 includes a light source 31, such as LED, positioned on an optical axis L2 of an objective lens 36, a target board 32, and a relay lens 33. This optical system 30 further includes a fixation lamp 34. During a zonular weakness measurement mode, the fixation target presenting optical system 30 is also used as a stimulus applying unit to apply a stimulus to guide the lens to move relative to the pupil of the examinee's eye. The target board 32 is used as a first fixation target for directing the visual axis of the examinee's eye in the straight-ahead direction during the zonular weakness measurement mode. Preferably, the target board 32 is changed to a target board having an opening at its center. The fixation lamp 34, which is a second fixation target for directing the visual axis of the examinee's eye upward (rotating the eyeball upward) during the zonular weakness measurement mode, is provided in an end portion of the target board 32. The fixation lamp 34 is placed at a position distant from the optical axis L2, at which the visual axis of the examinee's eye (optical axis) can move by a predetermined agree in a predetermined direction. The direction and the angle of movement are set to such that the lens of the examinee's eye can be wobbled when the eye gazing the fixation lamp 34 is turned to gaze the target board 32. In the present embodiment, the fixation lamp 34 is secured to the end portion of the target board 32 so that the visual axis of the examinee's eye moves by about 10 degrees in an elevation angle direction. The target board 32 and the fixation lamp 34 are integrally moved along the optical axis L2 by a drive mechanism (not illustrated in the drawings) including a motor and a sliding device. The target board 32 is thus moved to fog the examinee's eye E during measurement of the eye refractive power.

The examinee looks at the target board 32 and the fixation lamp 34 through the measurement window 4a. To induce a larger movement of the examinee's eye when the zonular weakness is to be measured, a fixation lamp may be provided on the measurement window 4a.

The controller 70 is connected to the measurement light source 11, light source 41, light source 44, imaging element 22, imaging element 52, light source 31, fixation lamp 34, drive mechanism for the target board, display 7, a switch unit 80 having a plurality of switches and being used for various measurement settings, a memory 75, XYZ drive unit 6, and others. A speaker 79 is connected to the controller 70 to emit a sound in a given tempo in order to guide the eye to gaze two points in turn during the zonular weakness measurement mode. The memory 75 stores therein images of the anterior segment (diaphanoscopic image) captured by the imaging element 52 at a predetermined frame rate during the zonular weakness measurement mode.

The switch unit 80 includes switches used to select one of the zonular weakness measurement mode and the eye refractive power measurement mode. To measure the eye refractive power, the fixation lamp 34 is turned off to make the examinee's eye gaze the fixation target of the target board 32. An image of the anterior segment of the examinee's eye illuminated by the light source 44 is captured by the imaging element 52 of the imaging optical system 50, and the image of the anterior segment thus captured is displayed on the display 7. The examiner observes the anterior segment image displayed on the display 7 and an alignment index image projected on the cornea by the light source 41, and moves the measuring unit 4 (the measurement optical system 10) by manipulating the joystick 5 to front, back, right, and left so that the examinee's eye and the measuring unit 4 are aligned with a predetermined positional relationship therebetween. When a trigger signal is thereafter inputted from the measurement start switch 5b, the eye refractive power measurement is started. The controller 70 detects the ring-shape image captured by the imaging element 22 to obtain the refractive power of the examinee's eye (sphere power S, astigmatic power C, astigmatism axis angle A). The measurement of the eye refractive power is a conventional operation, therefore, will not be described in any further detail.

The zonular weakness measurement mode is described below. The zonular weakness has a correlative relationship with the moving speed of the lens that follows the movement of the examinee's eye when moved. In the case of zonule strong enough as seen in a healthy subject, the lens following the motion of the eye moves at a very high moving speed. In the case of weak zonule, on the other hand, the moving speed of the lens slows down depending on the zonular weakness. Thus, the zonular weakness can be determined based on a lens position changing when the examinee moves his/her eye. To measure the zonular weakness, images of the anterior segment, which are captured after the stimulus is applied to guide the lens to move relative to the pupil of the examinee's eye, are image-processed to obtain positional information of a characteristic point of the lens, the mobility of the lens relative to the pupil when the lens returns to a pre-stimulus status is detected, and the zonular weakness is determined based on the detected mobility. Preferably, the zonular weakness is determined by obtaining the moving speed of the lens when returning to the pre-stimulus status. More simply, the zonular weakness is determined by detecting the mobility of the lens when returning to the pre-stimulus status based on whether a position of the characteristic point of the lens relative to a predetermined reference position of the pupil is included in a predetermined amount.

A stimulus applying unit which applies the stimulus for moving the examinee's eye is preferably a fixation target presenting unit configured to move the visual axis of the examinee's eye. For example, a first fixation target positioned in a first direction is switched to a second fixation target positioned in a second direction having an angle different from that of the first direction to rotate the eyeball by changing a fixation direction of the examinee's eye. Then, the zonular weakness is determined based on the images of the anterior segment captured then. The movement of the lens can be measured by image-processing the lens in the anterior segment images and extracting the image processing result.

With the device in this embodiment, the examinee's eye is guided to alternately gaze two fixation lamps (fixation targets) having different height positions to rotate the eyeball in a certain direction by a predetermined amount, and a positional change of a characteristic site in the lens is obtained based on at least two images of the anterior segment captured before, after, and around the movement of the eyeball (examinee's eye) or after the eyeball movement. The at least two images of the anterior segment captured before, after, and around the eyeball movement includes images captured before and after the eyeball movement, during the eyeball movement, before and during the eyeball movement, and during and after the eyeball movement. The positional change of the characteristic site in the lens is preferably calculated as the moving speed of the lens. A cataract operation on an eye with weak zonule needs to be carefully performed. In the description given below, an eye with a clouded lens affected by cataract that needs to be subjected to a cataract operation is to be examined in the zonular weakness measurement mode.

Figure 3A:
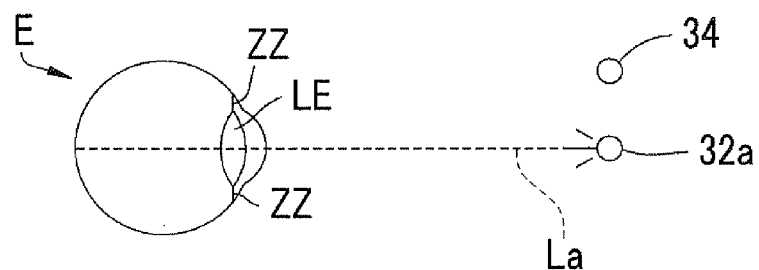
FIG. 3A is a schematic view to explain a relationship among rotation of an eyeball, movement of a lens, and zonular weakness.
Figure 3B:
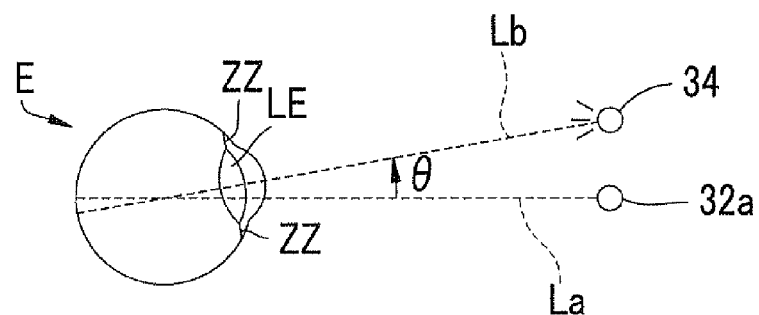
FIG. 3B is another schematic view to explain the relationship among rotation of an eyeball, movement of a lens, and zonular weakness.
Figure 3C:
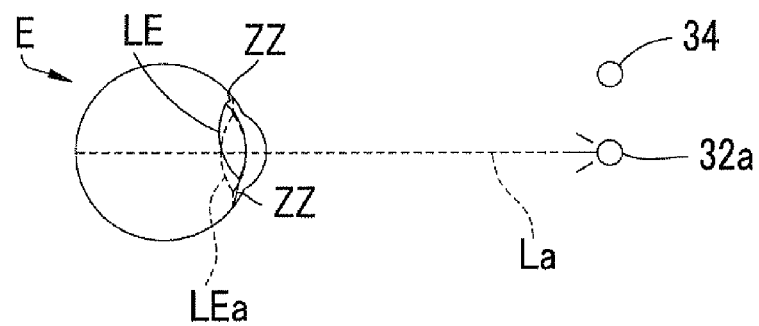
FIG. 3C is another schematic view showing the relationship among rotation of an eyeball, movement of a lens, and zonular weakness.

FIGS. 3A to 3C are schematic views to explain a relationship among the eyeball rotation, movement of the lens when the examinee's eye changes the direction of its visual axis (when the examinee's eye moves), and the zonular weakness. As illustrated in FIGS. 3A to 3C, Zinn's zonule ZZ of the examinee's eye E has an end fixed to the ciliary body (not illustrated in the drawings) and the other end fixed to the equator of a lens LE. The zonule ZZ is uniformly present in an outer periphery of the lens LE. Though not described in detail, the tension of the zonule ZZ is increased and released as the ciliary muscle of the ciliary body contracts and relaxes, and the thickness of the lens LE is accordingly changed.

The examinee's eye is first directed to gaze a fixation target 32a positioned in a first direction La which is a direction straight ahead of the eye as illustrated in FIG. 3A. The fixation target 32a is formed by the opening formed in the target board 32 illuminated by the light source 31.

As illustrated in FIG. 3B, the light source 31 for illuminating the fixation target 32a is turned off and the fixation lamp 34 positioned in a second direction Lb different from the first direction La is turned on to guide the visual axis of the examinee's eye to the fixation lamp 34, so that the examinee's eyeball is rotated upward by a predetermined angle. An angle θ of the visual axis direction Lb of the examinee's eye guided by the fixation lamp 34 relative to the visual axis direction La of the examinee's eye guided by the fixation target 32a is, for example, 10 degrees. When the angle θ by which the visual axis of the examinee's eye is guided is set to a fixed angle, the angle of rotation of the eyeball is constant, and the positional change of the lens can be measured under the same conditions.

After the examinee's eyeball is rotated upward, the fixation target 32a is turned on and the fixation lamp 34 is turned off to guide the visual axis of the examinee's eye to the fixation target 32a in the straight-ahead direction as illustrated in FIG. 3C. As the visual axis is thus guided, the lens LE moves downward in association with the rotation of the examinee's eye. In the case of an eye with weak zonule, however, the lens LE fails to return to an expected position by following the eyeball rotation, but slowly moves downward.

As a means for timely switching the visual axis direction of the examinee's eye between the straight-ahead direction La and the upper direction Lb, a clicking sound is generated from the speaker 79 to notify the examiner of the timing of switching the direction. For example, the fixation target 32a and the fixation lamp 34 are turned on and off in turn per second, and the timing of generating the clicking sound is synchronized the on/off timing. The fixation target 32a is switched to the fixation lamp 34 in sync with a first clicking sound, (a state in FIG. 3B), and the fixation lamp 34 is switched to the fixation target 32a in sync with a second clicking sound. The examinee is notified in advance that the fixation target 32a in the straight-ahead direction is switched to the fixation lamp 34 in the upper direction in sync with a clicking sound and then the fixation target 34 is switched to the fixation target 32a in the straight-ahead direction in sync with a next clicking sound, and the examinee is asked to change the visual axis direction in accordance with which of the fixation targets is turned on. Accordingly, the examinee's eye can be rotated (wobbled) by a given angle in a given tempo to move the lens.

When the diaphanoscopic image of the anterior segment is used to obtain the positional information of the moving lens associated with the rotation of the examinee's eye, the positional information can be obtained very accurately. During the zonular weakness measurement mode, as in the measurement of the eye refractive power, when a measurement start signal of the measurement start switch 5b is inputted after completion of the alignment of the examinee's eye, the light source 44 for illuminating the anterior segment is turned off and the light source 11 for capturing the diaphanoscopic image is turned on. When the light source 11 is turned on, infrared light is projected on the fundus through the pupil, and the lens is illuminated from behind by the light reflected from the fundus. Thus, the imaging element 52 of the imaging optical system 50 captures the diaphanoscopic image of the examinee's eye.

A diaphanoscopic image A is displayed on a screen of the display 7 shown in FIG. 2. In the diaphanoscopic image A, a bright image is obtained from the interior of a pupil Pu by the light reflected from the fundus, whereas a dark image is obtained from a clouded site C of the lens affected by cataract. The clouded site C can be used as the characteristic point (characteristic site) for identifying the position of the lens. The clouded sites C are dotted in the lens like clouds or present all over the lens. When the diaphanoscopic image A is image-processed by, for example, binarizing to extract the characteristic point of the clouded site C, the image processing result can be used as information for positionally identifying the lens.

In response to the trigger signal outputted to start the measurement, the fixation target 32a positioned straight ahead of the examinee's eye is turned off and the fixation lamp 34 in the upper direction is turned on, as illustrated in FIGS. 3A to 3C. After a given period of time (for example, one second) passes, the fixation target 32a is turned on in sync with the clicking sound. In response to the measurement-start trigger signal, the controller 70 fetches (stores) the diaphanoscopic images A captured by the imaging element 52 into the memory 75 at given time intervals (for example, at every ⅟₃₀ second of the imaging frame rate). The fetch of the diaphanoscopic images A should be completed in a certain period of time (for example, two seconds) from the switching timing of the fixation target 32a (FIG. 3C) in view of delay of the lens movement due to the zonular weakness and time lag of the visual axis movement of the examinee's eye.

Figure 4A:
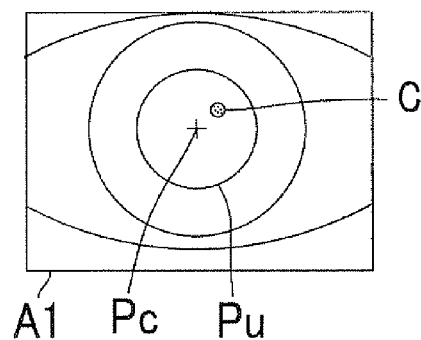
FIG. 4A is a diagram to explain measurement of a moving speed of the lens.
Figure 4B:
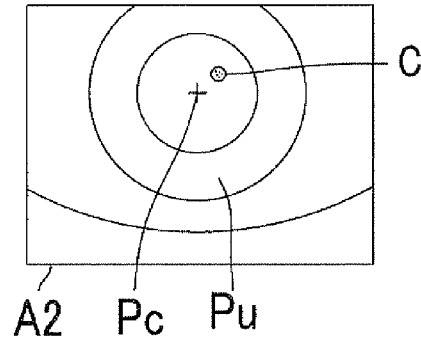
FIG. 4B is another diagram to explain measurement of the moving speed of the lens.
Figure 4C:
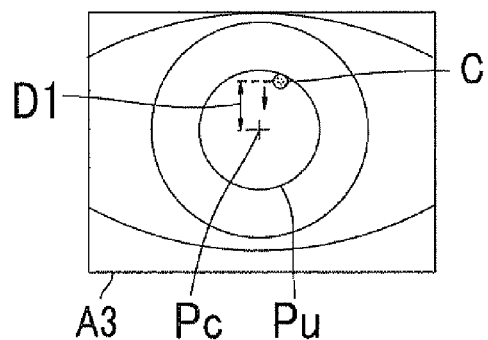
FIG. 4C is another diagram to explain measurement of the moving speed of the lens.
Figure 4D:
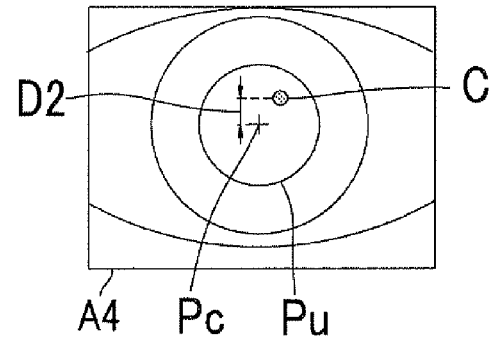
FIG. 4D is another diagram to explain measurement of the moving speed of the lens.

FIG. 4A shows an example of an anterior segment image (diaphanoscopic image) A1 when the visual axis direction of the examinee's eye is directed toward the fixation target 32a immediately after the start of measurement (a state in FIG. 3A). To simplify the explanation, the clouded site C is illustrated as one circle in the anterior segment image A1. In reality, a plurality of clouded sites is doted at different positions in the lens or spread in a part of the lens as shown in FIG. 2. FIG. 4B shows an anterior segment image A2 when the fixation lamp 34 is turned on again and the eyeball of the examinee's eye is thereby directed upward (a state in FIG. 3B). FIG. 4C shows an anterior segment image A3 when the fixation target 32a is turned on again and the visual axis of the examinee's eye is thereby directed back in the straight-ahead direction (a state in FIG. 3C). In the case of weak zonule, the lens failing to immediately follow the eyeball rotation does not return to the earlier status, leaving the clouded site C on the upper side of the pupil. FIG. 4D shows an anterior segment image A4 after the moving lens in the status of the anterior segment image A3 returns to the same status as shown in FIG. 4A. The anterior segment images A1 to A4 are obtained in conjunction with switching to and from the fixation lamp 34 and the fixation target 32a.

Whether the examinee' is moving (rotating) his/her eye in response to switching between the fixation target 32a and the fixation lamp 34 is detected from the images of the anterior segment obtained by the imaging element 52. For example, the pupil position (pupil center) included in the anterior segment image A1 is detected while the examiner's eye is gazing the fixation target 32a. When the pupil position (pupil center) is moved upward by at least a predetermined amount as shown in the anterior segment image A2 when the fixation lamp 34 is turned on, it is detected that the examinee moves his/her eye under the guidance of the fixation lamp 34. When the pupil position (pupil center) returns to substantially the same position as that of the anterior segment image A1 as shown in the anterior segment image A3, it is detected that the examinee moves his/her eye under the guidance of the fixation target 32a. When a detection result of the eye movement is fully utilized, the images of the anterior segment for use in determination of the zonular weakness can be very accurately obtained.

The moving speed of the lens is calculated based on the positional change of the same clouded site C between two images captured like the anterior segment images A1 to A4 in FIG. 4, and time points when the images are obtained. For example, the positions of the clouded site C relative to a pupil center Pc are obtained in the images stored in the memory 75 after the fixation target 32a is turned on again and the examinee's eye directed upward is thereby directed in the straight-ahead direction. Then, the following images are extracted; image A4 where the positional change of the clouded site C is no longer detected, and image A3 where the clouded site C has moved by a largest moving distance in the vertical direction (direction of the eyeball rotation) relative to the position of the clouded site C identified in the image A4. Next, a moving distance ΔD is calculated based on a distance D1 of the clouded site C from the pupil center Pc of the image A3 and a distance D2 of the clouded site C from the pupil center Pc of the image A4. Further, a time interval ΔT at which the images A3 and A4 are obtained is calculated. When the time interval ΔT and the moving distance ΔD of the clouded site C are thus obtained, a moving speed V of the lens can be calculated.

The pupil center Pc can be obtained by subjecting an edge of the pupil Pu to a conventional image processing such as binarizing. The position of the clouded site C can also be obtained by a conventional image processing such as binarizing.

The moving speed V of the lens is preferably calculated from two images; one obtained immediately after the eyeball is rotated and returns to the prior status and the other obtained when the movement of the lens is almost over. However, as far as two images extracted during the movement of the lens are available, the moving speed V of the lens can be calculated from the positional change of the lens and the time interval between the two images.

When the moving speed V of the lens is thus calculated, the controller 70 determines the zonular weakness, and a determination result thus obtained is displayed on the display 7. The moving speed V of the lens is slower as the zonule is weaker. For example, the zonular weakness zonule is determined by different levels defined on the basis of a healthy subject as a standard level, such as Level 1, Level 2, Level 3, . . . , as the moving speed V of the lens is slower. The zonular weakness may be determined by at least two levels; a normal level and a level needing particular attention during a cataract operation.

In the above explanation, the moving speed V of the lens is used to determine the zonular weakness. The zonular weakness may be more easily determined based on a moving distance of characteristic point of the lens relative to a reference position of the pupil between two images of the anterior segment obtained at a given time interval during the movement of the examinee's eye.

The zonular weakness may also be determined based on whether a positional change of the characteristic point of the lens between at least two images of the anterior segment before and after the movement of the examinee's eye is included in a predetermined amount. For example, the position of the clouded site C, which is a characteristic point in the anterior segment image A1 in FIG. 4A before the examinee's eye moves (the position relative to the pupil center Pc), is defined as a reference position. Then, the position of the same characteristic point in the anterior segment image A3 in FIG. 4C after the examinee's eye once moved upward returns to the original position (the position relative to the pupil center Pc) is obtained. The thus obtained position is then compared to a position of a characteristic point in an eye with zonule strong enough (an eye that does not need particular attention during a cataract operation). In the case where the position of the characteristic point relative to the pupil center Pc is larger than that of the normal eye (i.e., in the case where the characteristic point of the lens is beyond a predetermined amount relative to the reference position), the zonular weakness is determined as a low level which needs particular attention during a cataract operation. The image of the examinee's eye before the movement may be an image of the examinee's eye in which the lens sufficiently follows the movement of the eye as illustrated in the anterior segment image A2 of FIG. 4B.

As described above, the zonular weakness can be quantitatively and objectively measured. The device in the present embodiment can quantitatively and easily evaluate the zonular weakness as compared to the conventional manner in which a doctor who cuts a patient's eye checks the mobility of a lens by touching the lens using a surgical appliance and determines the zonular weakness. Because the device allows a doctor to measure the zonular weakness without any physical contact, the doctor can accurately ascertain the zonular weakness in a patient's eye before the doctor performs a cataract operation. This helps the doctor to schedule the operation in a time-efficient manner. A cataract operation performed on a patient with weak zonule often results in a lengthy operation as compared to a patient with zonule strong enough because a doctor needs to carefully remove the nucleus of lens to avoid the occurrence of any complications caused by, for example, accidental drop of the dislocated lens in the vitreous chamber. A doctor may have to perform a number of cataract operations in a day, in which case he/she can estimate the duration of operation for each patient by knowing beforehand the patient's weakness of zonule, allowing the doctor to suitably schedule the operations.

The present invention is not necessarily limited to the above embodiment but can be variously modified. For example, in the above explanation, the controller 70 identifies the clouded site which is the characteristic point indicating the position of the lens through the image processing. As an alternative, at least two images of the anterior segment may be displayed on the display after a series of images of the anterior segment are obtained so that an examiner identifies the characteristic point using an input device. In that case, the examiner preferably visually identifies the characteristic point using GUI (Graphical User Interface).

The image of the anterior segment captured during the zonular weakness measurement mode preferably includes at least a pupil portion. However, an image of the anterior segment captured otherwise is acceptable as far as the movement of the lens of the examinee's eye E can be calculated. For example, an image of the anterior segment in which a part of the pupil is missing (for example, an upper part is missing) is image-processed by the controller 70 to estimate the pupil circle, and the pupil center is obtained from the estimated pupil circle to perform the processing described above.

The moving speed of the lens can be obtained as far as two images of the anterior segment (diaphanoscopic images) are obtained. An alternative way of obtaining the moving speed of the lens of the examinee's eye is achieved by calculating a plurality of moving speeds between three or more images of the anterior segment, and then averaging the thus obtained moving speeds of the lens. Further, another alternative way of calculating the moving speed of the lens is achieved by displaying the images of the anterior segment stored in the frame memory in one measuring operation on the display monitor in the form of thumb nails to allow an examiner to choose two images of the anterior segment. In that case, the images of the anterior segment are preferably captured continuously at a predetermined frame rate, so that a time difference between the two images of the anterior segment arbitrarily selected can be uniquely defined.

To detect the mobility of the lens relative to the pupil when the lens returns to the pre-stimulus status, the diaphanoscopic image obtained by illuminating the lens from behind is preferably used. To examine an eye affected by cataract with severely clouded lens, an anterior segment illuminating optical system configured to illuminate the lens from ahead of the examinee's eye using a visible light source may be provided, in which case images of the anterior segment illuminated by the illuminating optical system and captured by the imaging optical system 50 are used.

Figure 5:
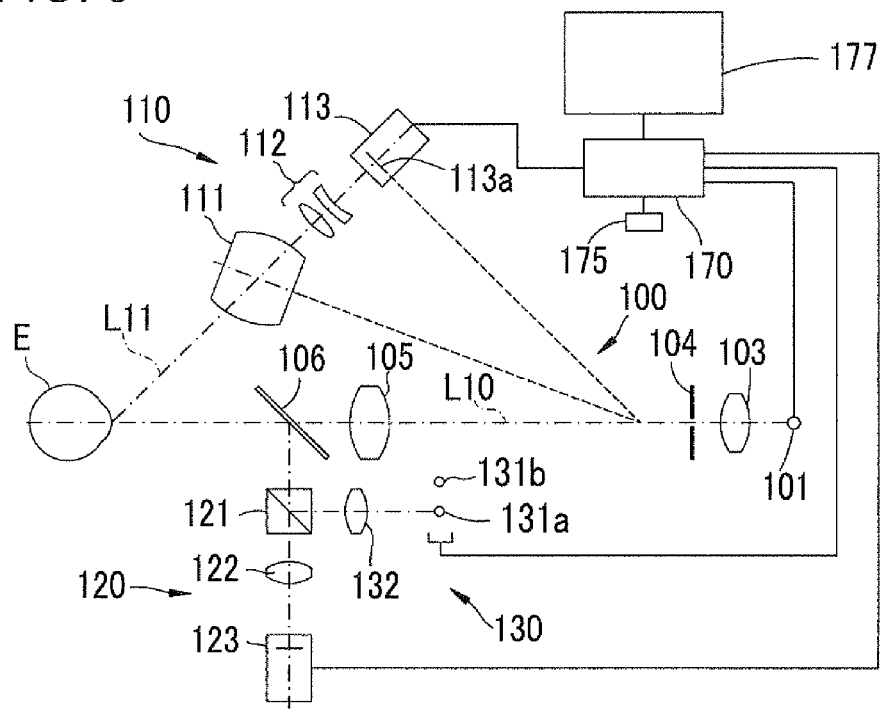
FIG. 5 shows a configuration example of an optical system to obtain a tomographic image of an anterior segment.

The image of the anterior segment of the examinee's eye obtained to detect the mobility of the lens relative to the pupil when the lens returns to the pre-stimulus status may be an image captured from straight ahead of the examiner's eye or a tomographic image obtained by optically cutting in cross section the anterior segment of the examinee's eye including the lens. FIG. 5 shows a configuration example of an optical system to obtain the tomographic image of the anterior segment of the examinee's eye.

In FIG. 5, the optical system includes an illuminating optical system 100 configured to optically cut the examinee's eye including the lens using a slit light, an imaging optical system 110 configured to capture an image of the lens optically cut in cross section from an oblique direction, an observation optical system 120 configured to capture an image of the anterior segment of the examinee's eye, and a fixation target optical system 130 configured to present a fixation target to the examinee's eye.

The illuminating optical system 100 includes, on an optical axis L10, a light source 101, which emits white visible light, a condenser lens 103, a slit aperture diaphragm 104, and a projection lens 105. Further, a dichroic mirror 106 is provided on the optical axis L10. A light flux emitted from the light source 101 is converged by the condenser lens 103 to illuminate the slit aperture diaphragm 104. The light flux confined in the shape of a thin slit by the slit aperture diaphragm 104 is projected on the examinee's eye E through the projection lens 105. As a result, the anterior segment of the examinee's eye E including the lens is illuminated so as to be optically cut by the white visible light.

On an optical axis L11 of the imaging optical system 110 are provided with a photographing lens 111, an anamorphic lens 112 for correcting an image distortion, and an imaging element 113. The optical axis L11 has a tilt angle of 45 degrees relative to the optical axis L10 of the illuminating optical system 100. The photographing lens 111 is positioned at a slant relative to the optical axis L11 so as to meet the Scheimpflug principle. More specifically, the photographing lens 111 is positioned so that a nodal line connecting an extension of the optical cross section of the anterior segment obtained by the slit illumination light and an extension of an imaging plane 113a of the imaging element 113 meets a line extended from a principal plane of the photographic lens 111. As a result of such an optical arrangement, the tomographic image captured by the imaging element 113 has a depth of focus that enables almost the whole image to come into focus. The illuminating optical system 100 and the imaging optical system 110 are integrally rotated about the optical axis L10 by a rotary mechanism not shown. As a result, the tomographic image can be obtained at any arbitrary angle.

The observation optical system 120 includes an imaging lens 122 and an imaging element 123, wherein the images of the anterior segment captured by the imaging element 123 from the straight-ahead direction are displayed on a display not shown. The fixation target optical system 130 includes a projection lens 132 on an optical axis divided by a beam splitter 121 and a point light source 131a both located on the optical axis of the observation optical system 120, and a point light source 131b located in a position not on the optical axis of the projection lens 132. The point light source 131a and the point light source 131b are provided in positions respectively corresponding to the fixation target 32a and the fixation lamp 34 in FIGS. 3A to 3C.

Figure 6:
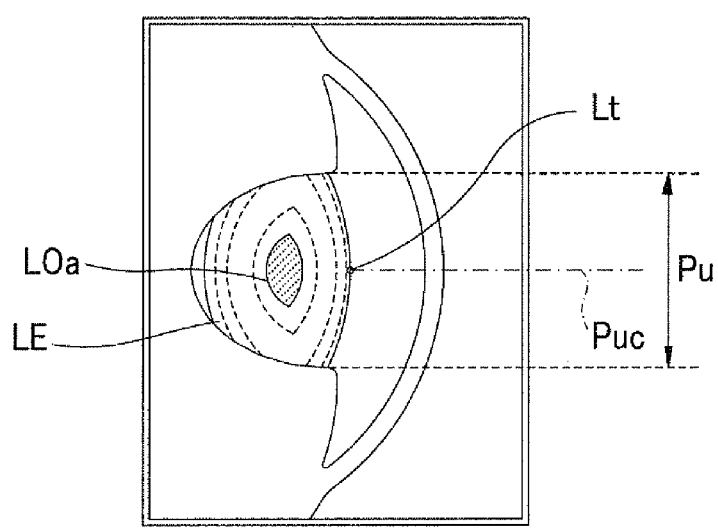
FIG. 6 shows an example of the tomographic image of the anterior segment.

According to the optical systems described above, the tomographic images of the examinee's eye captured by the imaging element 113 are inputted to a controller 170 and then displayed on a display 177. The tomographic images of the examinee's eye are also stored (fetched) in a memory 175. FIG. 6 shows an example of the tomographic image of the examinee's eye captured by the imaging element 113, which is a tomographic image of the lens LE optically cut in the pupil from its front to back surface. In the case of an eye with rather advanced cataract, layers of the nucleus of lens are observed as differences in the brightness distribution as illustrated with dotted lines in lens LE in FIG. 6, or the clouded sites are observed as differences in the brightness distribution relative to any other parts around the clouded sites.

When the signal of the measurement start switch is inputted after the examinee's eye and the optical systems are aligned so as to meet a predetermined positional relationship during the zonular weakness measurement mode, one of the point light sources 131*a* and 131*b* of the fixation target optical system 130 is turned off and the other is turned on to apply the stimulus to guide the lens move relative to the pupil in a manner similar to the illustrations of FIGS. 3A to 3C. Accordingly, the examinee's eyeball is rotated to be directed upward and straight ahead. The tomographic images captured by the imaging element 113 are stored in the memory 175 at given time intervals. Then, information of the movement of the lens is obtained by the controller 170 from the tomographic images after the examinee's eye directed upward is rotated to be directed straight ahead. Preferably, the controller 170 calculates the moving speed of the lens based on positional information of the characteristics point of the lens obtained by processing at least two tomographic images and a time interval at which the two tomographic images are captured. To identify the position of the lens, the brightness distribution of the nucleus of lens is image-processed, and the center layer of the lens is identified as the same characteristic point in the respective images. Alternatively, same clouded sites in respective images are identified as characteristic point. The position of the lens can be detected as a position relative to the center of the pupil Pu. When the same characteristic point in the respective images is identified and the positional information of the lens in the respective images is obtained, the moving speed V of the lens is calculated based on the time points when the images are respectively captured. Then, the zonular weakness is determined by different levels such as Level 1 to Level 4 based on the calculated moving speed V.

Figure 7:
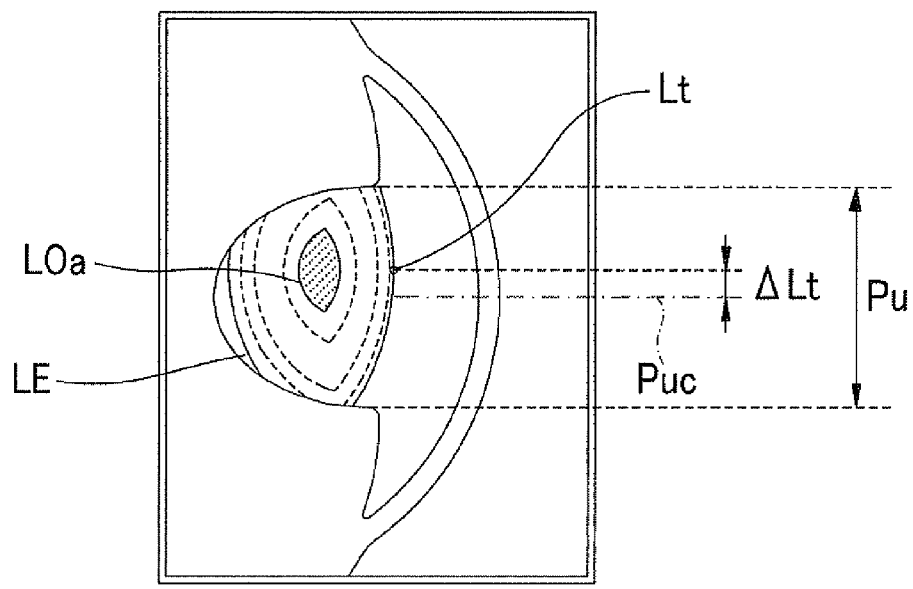
FIG. 7 shows an example of the tomographic image immediately after an examinee's eye directed upward is rotated to be directed straight ahead.

To simplify the determination, whether the position of the characteristic point in the lens is included in a predetermined amount is detected as the mobility of the lens relative to the pupil when the lens returns to the pre-stimulus state, and the zonular weakness is determined based on a detection result. FIG. 7 is an example of the tomographic image immediately after the examinee's eye directed upward is rotated to be directed straight ahead. A center layer LOa of the lens in FIG. 6 is at a position substantially equal to a center Puc of the pupil Pu. In contrast, a center layer LOa n FIG. 7 is at a position displaced from the center Puc of the pupil Pu. Based on this displacement amount, the zonular weakness is determined.

In the case of the tomographic image of the lens, a center Lt on a front surface curve of the lens can be used as the same characteristic point of the lens in different images. When the center Lt of the front surface curve and the center Puc of the pupil Pu are image-processed, the moving distance of the lens between two images can be calculated. The moving speed of the lens is calculated or whether the position of the moved lens is included in the predetermined amount is calculated to determine the zonular weakness.

In place of the above explained embodiment, another configuration may be adopted in which tomographic images of the anterior segment obtained by use of an optical coherence tomography (OCT) device is used to determine the zonular weakness. For example, the characteristic site of the lens may be extracted from the tomographic images of the anterior segment through an image processing to calculate the moving speed of the whole lens. The optical coherence tomography device includes an irradiation optical system configured to irradiate a measurement light emitted from a light source, which emits a light flux with a low-coherent length, on the examinee's eye, and a coherent optical system configured to receive interference light obtained by synthesizing reference light generated by splitting the light emitted from the light source with reflection light of the measurement light irradiated on the examinee's eye using a photo-receiving element, wherein the tomographic image of the examinee's eye is obtained based on a result obtained from the light received by the photo-receiving element, JP 2007-37984A and JP 2006-116028A disclose the technical features that can be employed in the optical coherence tomography device. The optical coherence tomography device is preferably configured to obtain the tomographic image by scanning the measurement light and receive the interference light divided into different frequency components. The coherent optical system provided in the optical coherence tomography device obtains the tomographic image from a signal received by the photo-receiving element such a line sensor. In the present specification, such a photo-receiving element is included as an example of the imaging element. The coherent optical system provided in the optical coherence tomography device is included in the imaging optical system.

In the above embodiment, the fixation target presenting optical system is used as the stimulus applying unit which applies the stimulus for guiding the lens of the examinee's eye to move relative to the pupil, wherein the visual axis of the examinee's eye is preferably guided by turning on the fixation targets in turn to rotate the eyeball by a given angle. Because the eyeball of the examinee's eye can be rotated physiologically by blinking, an image immediately after the blinking may be obtained. To obtain such an image, the controller 70 can automatically detect an opening state of the eye by image-processing the obtained image. Based on an eye-opening detection signal, the controller 70 obtains images of the anterior segment when the examinee moves his/her eye, and thereby determines the zonular weakness based on the obtained images of the anterior segment.

The anterior segment image obtained after completion of the alignment is defined as a reference image. The controller 70 compares the anterior segment image obtained in real time at a given frame rate to the reference image to determine whether the pupil, for example, is covered with an eyelid. Then, a signal indicating that the pupil can be imaged with the eyelid opened is used as a trigger to start the measurement. Accordingly, the measurement can be performed between blinking of the eye.

The movement of the examinee's eye (eyeball rotation) is not necessarily directed upward but may be directed downward, rightward, leftward, or in any given direction to guide the lens to move. Further, the movement of the examinee's eye (lens) is not necessarily guided by the fixation target but may be caused when the examinee blinks his/her eye on purpose or by an impact on the examinee's head. For example, a drive unit configured to move the face support unit 2 upward and downward is provided as the stimulus applying unit to forcibly move the eye. The movement of the examinee's eye is detected by a signal outputted from the drive unit which moves the face support unit 2.

To determine the zonular weakness, two images of the anterior segment associated with the movement of the eye are preferably used. To simplify the determination, the positional change of the lens may be obtained from one image of the anterior segment. For example, the center Lt of the front surface curve of the lens is generally at a position substantially equal to the center Puc of the pupil Pu prior to the movement of the examinee's eye as illustrated in FIG. 6. When the examinee moves his/her eye, a positional change ΔLt of the center Lt on the front surface curve of the lens relative to the center Puc of the pupil Pu can be detected from such an image of the anterior segment as illustrated in FIG. 7. The zonular weakness can be determined based on whether the positional change ΔLt stays within a predetermined amount. Moreover, the zonular weakness can be determined by different levels depending on the dimension of the positional change ΔLt.

The determination technique which uses one image of the anterior segment is not only applicable to the tomographic image but is also applicable to the front image or the diaphanoscopic images as illustrated in FIGS. 3A to 3C. For example, in the case where the positional relationship of the clouded site C relative to the pupil center Pc is known in advance before the eye movement as illustrated in FIG. 3A, the image A3 after the eye movement (FIG. 3C) is obtained. Then, the zonular weakness can be determined based on the positional relationship of the clouded site C relative to the pupil center Pc.

The present invention is not limited to the above embodiment and may be embodied in other specific forms without departing from the essential characteristics thereof.

DESCRIPTION OF THE REFERENCE SIGNS

10 Eye refractive power measuring optical system
10a Light projecting optical system
10b Photo-receiving optical system
30 Fixation target presenting optical system
32 Target board
32a Fixation target
34 Fixation lamp
44 Anterior-segment illumination light source
50 Imaging optical system
52 Imaging element
70, 170 Controller
100 Illumination optical system
110 Imaging optical system
113 Imaging element
120 Observation optical system
130 Fixation target optical system
131a, 131b Point light source
LE Lens
Pc Pupil center
Pu Pupil

The invention claimed is:

1. An ophthalmic device to measure weakness of Zinn's zonule of an examinee's eye, the device comprising:
an illuminating unit arranged to illuminate the examinee's eye including a lens;
an imaging unit including an imaging element and arranged to capture an image of an anterior segment illuminated by the illuminating unit; and
a determination unit arranged to process the image of the anterior segment captured by the imaging unit after applying a stimulus to guide the lens to move and change a visual direction of the examinee's eye, the determination unit being further configured to obtain positional information of a characteristic point of the lens to detect mobility of the lens relative to the pupil when the lens returns to a pre-stimulus status, and determine the zonular weakness based on the detected mobility of the lens correlated to a moving speed in the up-down and right-left directions with respect the examinee's eye, the examinee's eye caused to change direction by applying the stimulus to introduce movement of the lens.

2. The ophthalmic device according to claim 1, wherein the determination unit image-processes at least two images of the anterior segment, calculates a moving speed of the lens when returning to the pre-stimulus status based on positional information of characteristic points of the lens in the respective images and a time interval at which the images are captured, and determines the zonular weakness based on the calculated moving speed.

3. The ophthalmic device according to claim 2, wherein the determination unit obtains at least two images of the anterior segment before and after the movement of the eye caused by the applied stimulus, during the movement of the eye, before and during the movement of the eye, or during and after the movement of the eye.

4. The ophthalmic device according to claim 1, wherein the determination unit detects the mobility of the lens when returning to the pre-stimulus status based on whether a position of the characteristic point of the lens relative to a predetermined reference position of the pupil is included in a predetermined amount to determine the zonular weakness.

5. The ophthalmic device according to claim 1, wherein the determination unit processes the image of the anterior segment to obtain a clouded site of the lens as the characteristic point.

6. The ophthalmic device according to claim 1, wherein the determination unit image-processes at least two images of the anterior segment captured by the imaging unit before and after application of the stimulus and extracts a predetermined characteristic point of the lens in each image to determine the zonular weakness based on whether a positional change of the characteristic point in each image is included in a predetermined amount.

7. The ophthalmic device according to claim 1, further including a memory for storing the image of the anterior segment captured by the imaging unit, the memory storing therein at least two images of the anterior segment before and after the movement of the examinee's eye caused by the applied stimulus, during the movement of the examinee's eye, before and during the movement of the examinee's eye, or during and after the movement of the examinee's eye,
wherein the determination unit image-processes the images of the anterior segment stored in the memory to obtain positional information of the characteristic point of the lens, and detects the mobility of the lens relative to the pupil when the lens returns to the pre-stimulus status.

8. The ophthalmic device according to claim 1, further including a stimulus applying unit arranged to apply the stimulus to guide the lens to move.

9. The ophthalmic device according to claim 8, wherein the stimulus applying unit includes a fixation target presenting unit having a fixation target for guiding a visual axis of the examinee's eye, the fixation target presenting unit being configured to switch the fixation target between a first direction and a second direction different from the first direction.

10. The ophthalmic device according to claim 1, further including:
an eye opening detecting unit arranged to detect opening of the examinee's eye after blinking of the eye based on the image of the anterior segment captured by the imaging unit, and
an image obtaining unit arranged to obtain the image of the anterior segment after application of the stimulus based on a detection signal outputted from the eye opening detecting unit.

11. The ophthalmic device according to claim 1, wherein the imaging unit has an optical axis for capturing an image of the examinee's eye from a direction straight ahead of the eye, and the imaging unit obtains a diaphanoscopic image in which the lens is illuminated from behind by illumination light of the illuminating unit or an image of the anterior segment in which the lens is illuminated from a direction straight ahead of the examinee's eye by the illumination light of the illuminating unit as the image of the anterior segment.

12. The ophthalmic device according to claim 1, wherein
the illuminating unit includes an illumination light source and a slit aperture to project slit light on the lens of the examinee's eye, and
the imaging unit has an optical axis for capturing an image of the examinee's eye from an oblique direction of the eye and captures a tomographic image of the lens optically cut in cross section by the slit light.

13. The ophthalmic device according to claim 1, wherein the imaging unit includes an optical coherence tomography device and obtains a tomographic image of the anterior segment including the lens.

14. The ophthalmic device according to claim 2, wherein the determination unit image-processes the at least two images of the anterior segment and calculates the moving speed in the up-down and right-left directions of the lens.

15. The ophthalmic device according to claim 1, wherein the determination unit is configured to obtain positional information of at least part of the lens by image processing of the image of the anterior segment.

16. The ophthalmic device according to claim 1, further comprising a display configured to display a result of the determined zonular weakness.

17. The ophthalmic device according to claim 16, wherein the zonular weakness is determined by different levels defined on a basis of a healthy subject.

18. The ophthalmic device according to claim 1, wherein the stimulus applying unit includes a fixation target presenting unit having a plurality of fixation targets located at different positions with respect to the up-down and right-left directions for guiding a visual axis of the examinee's eye, the fixation target presenting unit being configured to switch the plurality of fixation targets to move the visual axis of the examinee's eye in the up-down and right-left directions.

* * * * *